(12) United States Patent
Kitaoka (10) Patent No.: US 8,175,810 B2
(45) Date of Patent: May 8, 2012

(54) SAMPLE PROCESSING APPARATUS AND SAMPLE PROCESSING METHOD

(75) Inventor: Atsushi Kitaoka, Kisarazu (JP)

(73) Assignee: Canon Kabushiki Kaisha, Tokyo (JP)

( * ) Notice: Subject to any disclaimer, the term of this patent is extended or adjusted under 35 U.S.C. 154(b) by 903 days.

(21) Appl. No.: 11/830,557

(22) Filed: Jul. 30, 2007

(65) Prior Publication Data

US 2008/0028871 A1 Feb. 7, 2008

(30) Foreign Application Priority Data

Aug. 4, 2006 (JP) ................................ 2006-213275

(51) Int. Cl.
*G01N 33/48* (2006.01)
(52) U.S. Cl. ............ 702/19; 707/999.103; 707/999.104; 706/45; 706/46; 436/147; 436/37; 422/65; 422/63; 422/66; 435/6; 435/287.2
(58) Field of Classification Search .................. None
See application file for complete search history.

(56) References Cited

U.S. PATENT DOCUMENTS 6,721,615 B2 * 4/2004 Fava et al. ..................... 700/99
2004/0259111 A1 * 12/2004 Marlowe et al. ................. 435/6

FOREIGN PATENT DOCUMENTS

| JP | 5-307039 | 11/1993 |
| JP | 2003-98180 | 4/2003 |

* cited by examiner

*Primary Examiner* — Sally Sakelaris
(74) *Attorney, Agent, or Firm* — Fitzpatrick, Cella, Harper & Scinto (57) ABSTRACT

A sample processing apparatus prevents samples and reagents from being degraded due to a prolonged waiting time other than for reaction and improves the operation efficiency of the apparatus. The apparatus includes a plurality of processing sections for causing at least two samples to react independently, an input/output terminal 15 for inputting the upper limit of the waiting time and the reaction time for each of the samples, a schedule management section for determining at least the clock time of introducing each of the samples, the processing section to be used for processing the sample and/or the waiting time for the sample, and a general control section for controlling the processing of the samples at the plurality of processing sections according to the determination by the schedule management section.

5 Claims, 8 Drawing Sheets

| SAMPLE ID | PRE-AMPLIFICATION SAMPLE CONTAINER | | | | AMPLIFICATION REACTION VESSEL | | | PRE-HYBRIDIZATION SAMPLE CONTAINER | | | | HYBRIDIZATION REACTION VESSEL | | |
|---|---|---|---|---|---|---|---|---|---|---|---|---|---|---|
| | | WAITING TIME UPPER LIMIT T11 | 4 | | | PROCESSING TIME T12 | 8 | | WAITING TIME UPPER LIMIT T13 | 5 | | | PROCESSING TIME T14 | 10 |
| | CONTAINER NO. | (EXPECTED) WAITING TIME T1 | (EXPECTED) INTRODUCING CLOCK TIME T2 | (EXPECTED) ENDING CLOCK TIME T3 | CONTAINER NO. | (EXPECTED) INTRODUCING CLOCK TIME T4 | (EXPECTED) ENDING CLOCK TIME T5 | CONTAINER NO. | (EXPECTED) WAITING TIME T6 | (EXPECTED) INTRODUCING CLOCK TIME T7 | (EXPECTED) ENDING CLOCK TIME T8 | CONTAINER NO. | (EXPECTED) INTRODUCING CLOCK TIME T9 | (EXPECTED) ENDING CLOCK TIME T10 |
| 1 | * | * | * | * | * | * | * | * | * | * | * | 25A | * | 6 |
| 2 | * | * | * | * | * | * | * | 24A | * | * | 1 | 25C | 1 | 11 |
| 3 | * | * | * | * | 23C | * | 2 | 24B | 2 | 2 | 4 | 25B | 4 | 14 |
| 4 | * | * | * | 1 | 23B | 1 | 2 | 24C | 4 | 2 | 6 | 25A | 6 | 16 |
| 5 | 22A | * | * | 2 | 23A | 2 | 9 | 24A | 2 | 9 | 11 | 25C | 11 | 21 |
| 6 | 22B | * | 1 | 5 | 23B | 5 | 10 | 24B | 4 | 10 | 14 | 25B | 14 | 24 |
| 7 | 22C | 4 | 5 | 9 | 23C | 9 | 13 | 24C | 3 | 13 | 16 | 25A | 16 | 26 |
| 8 | 22A | 4 | 7 | 11 | 23A | 11 | 17 | 24A | 4 | 17 | 21 | 25C | 21 | 31 |
| 9 | 22B | 4 | | | 23B | | 19 | 24B | 5 | 19 | 24 | 25B | 24 | 34 |

SAMPLE PROCESSING APPARATUS AND SAMPLE PROCESSING METHOD

BACKGROUND OF THE INVENTION

1. Field of the Invention

This invention relates to a processing apparatus for automatically conducting a biochemical reaction processing. More particularly, the present invention relates to a sample processing apparatus and a sample processing method to be used in gene examinations for detecting a nucleic acid extracted from a sample.

2. Description of the Related Art

Gene analyses using a test piece such as a DNA microarray or a DNA chip have been and being popularly conducted in recent years. A DNA microarray is a type of detection device prepared by arranging DNA probes of a number of different kinds on and anchoring them to the surface of a substrate, which may be a piece of slide glass or a silicon substrate, as so many probe spots to form a matrix. Then, the DNA microarray and an analyte that is labeled typically with a fluorescent dye are brought into contact with each other under hybridizing conditions. The labeling substance is fixed onto the DNA microarray by way of a probe nucleic acid when the DNA microarray and the analyte contain nucleic acids that give rise to a hybridization reaction. Then, the type of the nucleic acids can be identified that gave rise to the hybridization reaction by detecting the position of the labeling substance on the DNA microarray where the hybridization reaction took place.

A typical processing flow of gene analysis shows a sequence of (1) extraction of a nucleic acid from a sample, (2) amplification of the extracted nucleic acid, (3) hybridization reaction of the amplified nucleic acid and a DNA microarray and (4) detection of the hybridization reaction. Of the above steps, the steps (1) through (3) require cumbersome operations of liquid handling and container handling for the sample and the reagent and hence there is a strong demand for automation from the viewpoint of saving both labor and time.

Several proposals have hitherto been made in attempts to realize automated biochemical reactions.

For example, Japanese Patent Application Laid-Open No. H05-307039 describes a technique of defining the processing time and the waiting time in each processing step as a function of the type of each sample. Then, priority is defined for each of the received samples in terms of the order of processing and the sample to be processed is selected according to the defined priority and the defined waiting time so that the detection process is started with the sample having the highest priority. The above-cited patent document discloses an antibody detection method of processing the sample having the highest priority among the samples that are ready for processing because of zero waiting time or the waiting time has already elapsed, during the waiting time of a preceding sample whose processing time has elapsed for the processing step. The above-cited method enables to effectively exploit the waiting time so as to process the sample with a different processing sequence or process some other samples or add a new sample on the way of the processing operation.

Japanese Patent Application Laid-Open No. 2003-098180 discloses a system for determining the timing of conveying a plurality of sample processing units that are linked to each other according to the idleness of the receiving place and the waiting place of each processing unit. The system can rationally distribute objects of conveyance in a simple manner and such a system can be configured with ease regardless of the number of linked sample processing units.

Apparatus equipped with processing units capable of processing a plurality of successive steps may typically involve labor saving and time saving arrangements for conducting biochemical reactions. Desirably, such apparatus can process a plurality of samples by means of a single processing unit to improve the processing efficiency.

Meanwhile, the timing of actually starting a reaction processing of each sample cannot be determined in a simple manner. A large number of samples may be brought in beyond the processing capacity of an apparatus or a small number of samples may be brought in so as to be processed sequentially with a small time lag. As many samples as the processing section can accommodate may be set for processing in the former occasion. In the latter occasion, however, the processing efficiency of the apparatus can fall to increase the total processing time of processing a large number of samples because the processing is conducted without utilizing the full processing capacity. Therefore, it is desirable that the processing section can process a plurality of samples independently at arbitrarily defined timings. In other words, it is necessary that the processing section is divided into a plurality of subunits that can operate independently.

When such an arrangement is employed, it is necessary to efficiently manage the schedule according to the sample processing situation in the apparatus in order to improve the processing efficiency of the apparatus. If the processing time of the steps is reduced in the future, more samples may need to be processed accordingly. In short, the importance of process scheduling will become much more important in the future.

From the viewpoint of samples, the results of examination can be affected by the time for which a sample is waiting for the processing. Therefore, if a sample and a reagent are held waiting in the apparatus, it is necessary to keep the sample and the reagent at low temperature or define the range of waiting time.

According to the above-cited Japanese Patent Application Laid-Open No. H05-307039, priority is defined for each of the samples received by the apparatus and the processing schedule is prepared for the plurality of samples. While this technique may be able to prevent the waiting time of a high priority sample from being prolonged, the waiting time of a low priority sample by conversely be prolonged. Additionally, when two or more than two samples are brought in with the same priority, it is not possible to prevent the waiting time from being prolonged.

According to the above-cited Japanese Patent Application Laid-Open No. 2003-098180, samples are brought to idle places by seeing the timing of conveyance, the waiting place and the receiving place for idleness. However, with this technique, the waiting time of a sample is long when there is not any idle place. The above-listed problems inevitably occur when samples are brought in without taking the processing capacity of the examination apparatus into consideration.

SUMMARY OF THE INVENTION

Therefore, an object of the present invention is to solve the above-identified problems and enable to compatibly improve both the operation efficiency of an apparatus and the accuracy of the results of processing.

As a result of intensive research efforts, the inventors of the present invention came to the following conclusion. Namely, the inventors of the present invention found that it is important to manage information on the possible maximum waiting time until the time of processing each sample in order to compatibly improve both the operation efficiency of an apparatus and the accuracy of the results of processing. Thus, the inventors of the present invention got to the conclusion that an effective measure lies in optimizing the processing schedule management and, if necessary, limiting the input of new samples to the apparatus.

Thus, according to the present invention, the above object is achieved by providing a sample processing apparatus including: a processing unit for processing samples including a plurality of processing sections having individual processing abilities, at least two of the plurality of processing sections being capable of independently performing processing operations; a memory for storing information on maximum waiting times for introducing samples into the processing sections; and a scheduling section for preparing a processing schedule for the samples according to the information on maximum waiting times.

For the purpose of the present invention, a sample refers to a living tissue, a nucleic acid, a protein or some other ingredients extracted from a living tissue or, in some cases, a mixture of a living tissue or ingredients thereof and a reagent. The maximum waiting time of a sample refers to the permissible maximum waiting time from the clock time when the sample is introduced into the processing apparatus to the clock time when the operation of processing the sample starts.

Thus, according to the present invention, both the operation efficiency of an apparatus and the accuracy of the results of processing can be compatibly improved. More specifically, according to the present invention, there will no longer be samples accumulated in the apparatus and a long waiting time that may adversely affect samples can be avoided.

Further features of the present invention will become apparent from the following description of exemplary embodiments with reference to the attached drawings.

DETAILED DESCRIPTION OF THE PREFERRED EMBODIMENTS

Now, embodiments of the present invention will be described in greater detail by referring to the accompanying drawings.

First Embodiment

The first embodiment of the present invention is a gene examination apparatus for identifying the nucleic acid in a sample by amplifying the nucleic acid extracted from the sample, causing the amplified nucleic acid to react with a DNA microarray and detecting the reaction product. The first embodiment will be described below.

Figure 1:
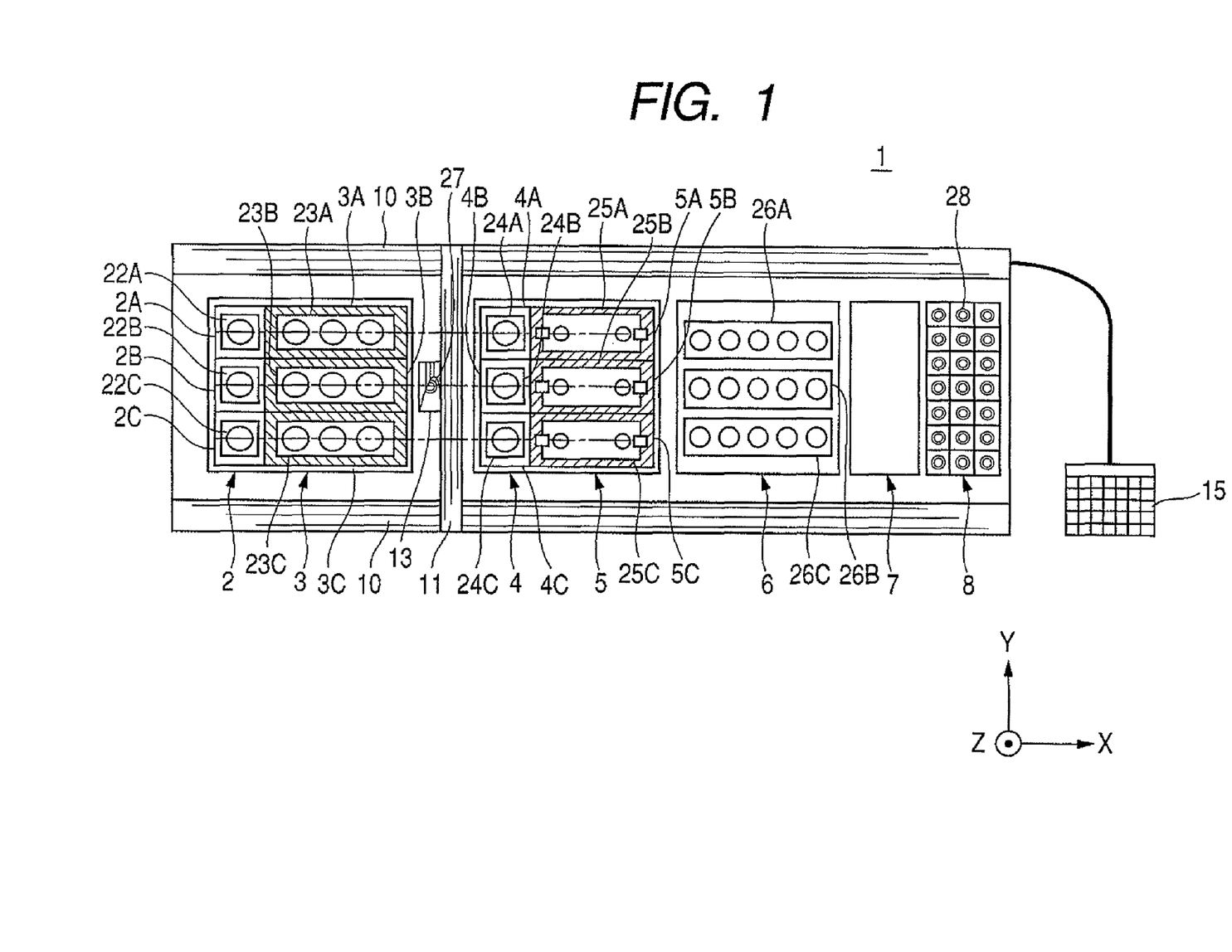
FIG. 1 is a schematic plan view of a first embodiment of gene examination apparatus according to the present invention.
Figure 2:
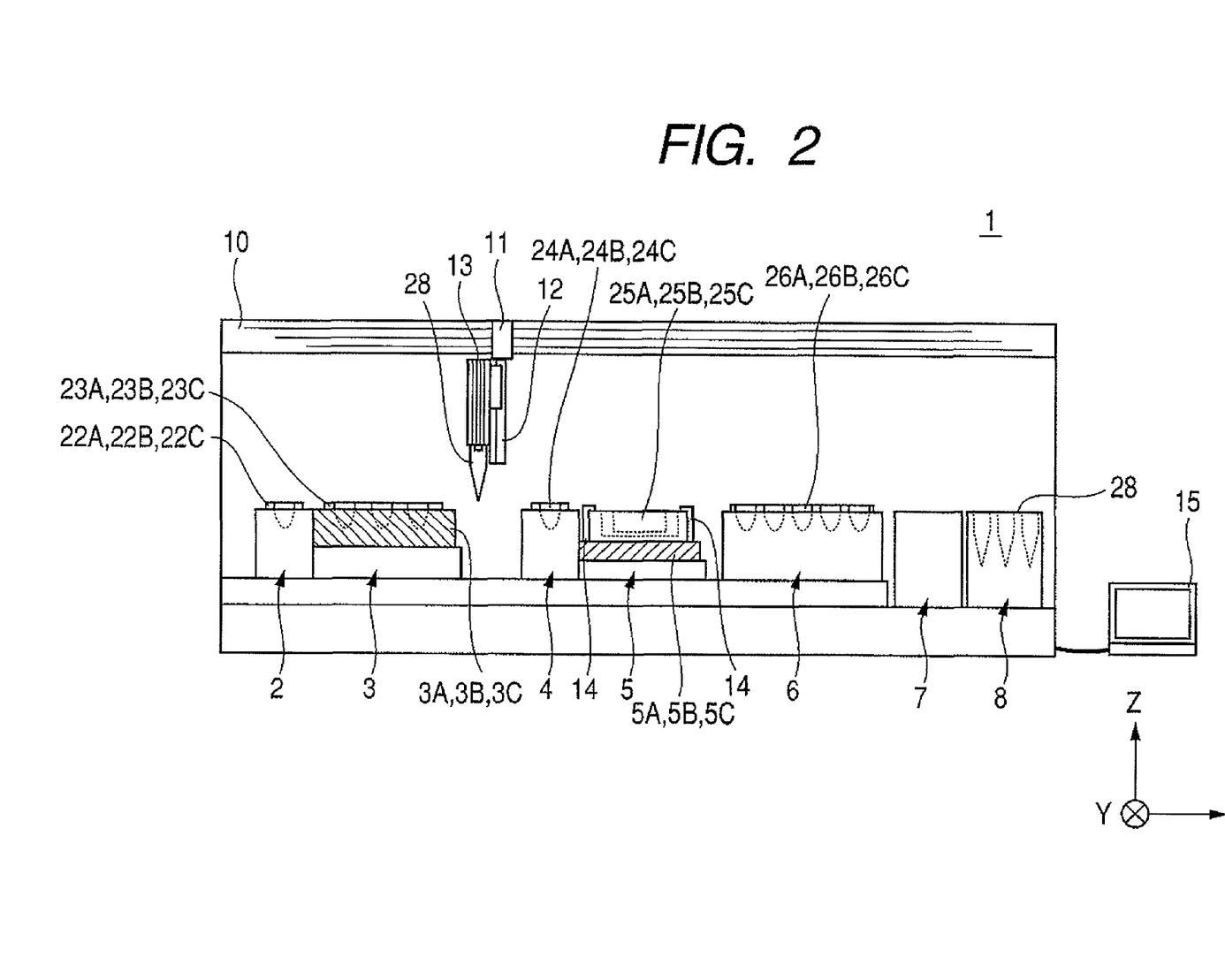
FIG. 2 is a schematic front view of the first embodiment of gene examination apparatus according to the present invention.
Figure 3:
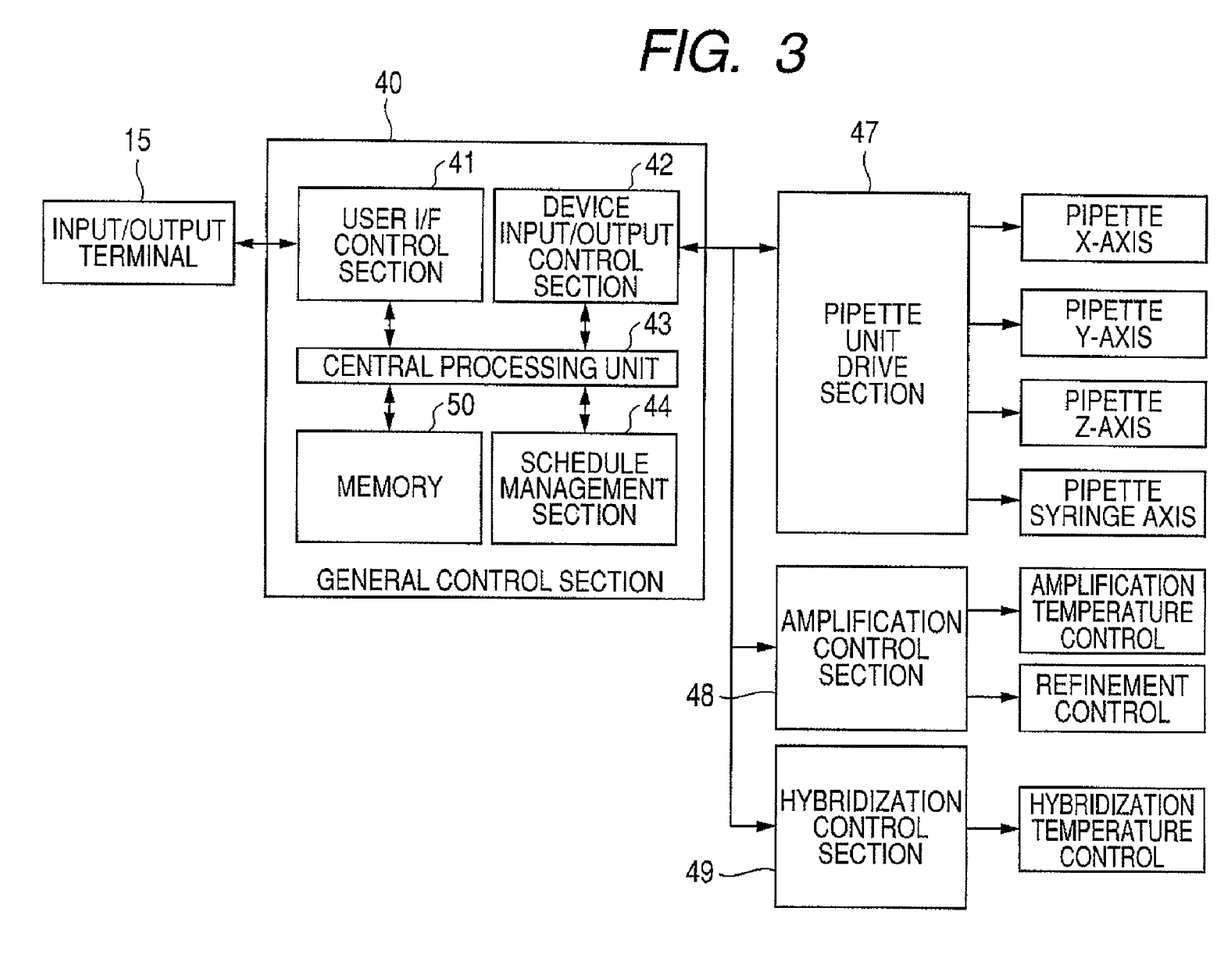
FIG. 3 is a schematic block diagram of the control system of the first embodiment of gene examination apparatus according to the present invention.

FIG. 1 is a schematic plan view of the gene examination apparatus as viewed from above. FIG. 2 is a schematic front view of the gene examination apparatus. FIG. 3 is a schematic block diagram of the control system of the gene examination apparatus.

The liquid containing a sample nucleic acid to be examined (to be referred to as sample nucleic acid liquid hereinafter) is PCR-amplified by amplification unit 3 and then the amplified sample nucleic acid is labeled by a fluorescent dye. Subsequently, the target sample nucleic acid is subjected to a hybridization reaction with a DNA microarray in hybridization unit 5. Thereafter, the DNA microarray is taken out from the gene examination apparatus 1 and the signal in the DNA microarray is detected by means of a fluorescence detector (not shown) that is independent from the gene examination apparatus 1.

Three lines of waiting sections and processing sections are provided in the gene examination apparatus 1 of this embodiment. Each line has a waiting section for accommodating a waiting sample and a processing section for processing the sample. The three lines can operate independently and will be referred to as A line, B line and C line hereinafter.

Referring to FIG. 1, each line is arranged in such a way that the processing proceeds from the −X side to the +X side in the X-direction. The A line, the B line and the C line are arranged from the +Y side to the −Y side in the mentioned order. A, B and C may be affixed in the following description of the lines and in the related drawings. For example, of the pre-amplification waiting places 2, the part located on the A line is denoted by 2A. As for containers, a pre-amplification sample container 22 arranged at a place on the A line is denoted by 22A. The term "unit" is used as in the expression of amplification unit 3. The parts 3A, 3B and 3C that constitute the amplification unit 3 may also be referred to as "units".

Liquid is transferred from a container to another container automatically by means of a pipette unit 13. The pipette unit 13 is provided with a 3-axes drive mechanism for the X-axis, the Y-axis and the Z-axis in the coordinate system illustrated in FIG. 1 and a syringe drive mechanism for driving the syringe section for the purpose of sucking and ejecting liquid. The pipette unit 13 is supported by a pipette unit X-axis guide 10, a pipette unit Y-axis guide 11 and a pipette unit Z-axis guide 12 so as to be movable in the directions of the three axes. In this embodiment, the pipette unit 13 is so adapted that a single pipette chip 28 is mountable there. As another mode, the pipette unit 13 may alternatively be so arranged that a plurality of pipette chips 28 are mountable. With such an arrangement, the pipette unit 13 is desirably so designed that pipette chips may be individually mountable and dismountable and the three lines may be independently operated for processing to characterize the present invention. Still alternatively, a gene examination apparatus according to the present invention may be provided with a plurality of independently drivable pipette units.

Additionally, the hybridization unit 5 is provided with a hybridization reaction vessel holder 14 for temporarily anchoring hybridization reaction vessels 25A, 25B and 25C that are reaction fields for hybridization reactions.

Still additionally, as illustrated in FIG. 3, various pieces of information input from input/output terminal 15, which is an input/output unit, are input to a general control section 40, which is a control unit, of the gene examination apparatus 1. The general control section 40 has a user I/F control section 41, a device input/output control section 42, a central processing unit 43, a memory 50 for storing information on the maximum waiting times of samples and a schedule management section 44 having a schedule preparation unit. The device input/output control section 42 operates to drive the pipette X-axis, the pipette Y-axis, the pipette Z-axis and the pipette syringe axis by way of pipette unit drive section 47. Additionally, the device input/output control section 42 controls the amplification temperature and the refinement of samples by way of amplification control section 48 and also controls the temperature of hybridization reaction by way of hybridization control section 49.

(1) Placement of Containers

The containers are placed at predetermined respective positions of the apparatus by the user before the start of an operation. More specifically, the pre-amplification sample containers 22A, 22B and 22C are placed at the pre-amplification sample waiting place 2 for temporarily holding samples and the amplification reaction vessels 23A, 23B and 23C are placed in the amplification unit 3. Additionally, the pre-hybridization sample containers 24A, 24B and 24C are placed at the pre-hybridization sample waiting place 4 for temporarily holding samples before hybridization reaction. Still additionally, the hybridization reaction vessels 25A, 25B and 25C are placed in the hybridization unit 5 and the reagent containers 26a, 26B and 26C are placed at the reagent depository 6, while pipette chips 28 are placed at the pipette chip depository 8. While containers are placed and collected manually by the user of the gene examination apparatus 1 of this embodiment, the apparatus is desirably provided with an automatic conveyance unit for automating the processing. Those skilled in the art can form such an automatic conveyance unit with ease by combining various appropriate units.

The reagents are put into the reagent containers 26A, 26B and 26C in advance by predetermined respective amounts necessary for the amplification reactions and the hybridization reactions that take place therein.

(2) Introduction of Samples

The samples, which may typically be bloods, are subjected to a nucleic acid extraction process in a processing apparatus that is separate from the gene examination apparatus 1 to prepare sample nucleic acid liquids. Then, the sample IDs of the samples to be introduced into to the gene examination apparatus 1 and the order of introducing them are input by way of the input/output terminal 15.

As the various pieces of information are input, the central processing unit 43 determines the pre-amplification sample container (one of the containers 22A, 22B and 22C) to be used and the expected introducible clock time (or prepares a processing schedule) according to the information on the samples stored in the memory 50 including information on the maximum waiting time of each of the samples in the apparatus and displays these pieces of information on the input/output terminal 15. The user introduces the sample nucleic acid liquid according to the information displayed on the input/output terminal 15. After introducing the sample nucleic acid liquid, the user inputs a message to the input/output terminal 15, telling that the introduction is completed.

The central processing unit 43 then determines the pre-amplification sample container that corresponds to the sample ID and the expected introducible clock time. At the same time, the central processing unit 43 determines the correspondence of the amplification reaction vessel, the pre-hybridization sample container and the hybridization reaction vessel and the predicted introducible clock times thereof. In other words, the central processing unit 43 books the pre-amplification sample container, the amplification reaction vessel, the pre-hybridization sample container and the hybridization reaction vessel with respective associated clock times before the sample is introduced into the gene examination apparatus 1.

The booking method that takes an essential part of the present invention will be described in greater detail hereinafter.

(3) Transfer of Sample Nucleic Acid Liquid to Amplification Reaction Vessel

The pipette unit 13 is moved to the pipette chip depository 8 and an unused pipette chip 28 is mounted on the pipette unit 13. Subsequently, the pipette unit 13 is driven to transfer the sample nucleic acid liquid from the pre-amplification sample container (e.g., assume here that it is the container 22A) containing the sample nucleic acid liquid to the left side well (to be referred to as 23B-L) in FIG. 1 of the booked amplification reaction vessel (e.g., assume here that it is the vessel 23B). Then, the pipette unit 13 is further moved to the reagent depository 6 and the PCR reagent is transferred from a predetermined well (e.g., the leftmost well of the reagent container 26A) to well 23B-L. A cycle of suction and ejection is repeated in the well 23B-L by using the pipette unit 13 to accelerate the mixing of the sample nucleic acid liquid and the reagent. After the transfer of the sample nucleic acid liquid, the used pre-amplification sample container 22A is replaced by an unused one at a predetermined timing.

(4) Amplification Step

The amplification unit 3 is adapted to amplify the nucleic acids by way of PCR, using the amplification reaction vessels 23A, 23B and 23C. The amplification unit 3 includes units 3A, 3B and 3C of the three lines that can operate independently. Each of the units 3A, 3B and 3C of the three lines is provided with a temperature block adapted to perform a thermal cycle and mechanism for controlling the refining operation of removing unnecessary objects from the amplification product. This embodiment adopts a nucleic acid adsorption/isolation system that employs magnetic silica beads as refiner and the amplification unit 3 of each line has a magnet (a permanent magnet or an electric magnet). However, the refiner that can be used for the purpose of the present invention is by no means limited to such a system and some other popularly known technique such as a technique using a column may alternatively be adopted.

Then, temperature block of the amplification unit (e.g., the unit 3B here) is driven at predetermined three temperatures including a denaturing temperature, an annealing temperature and an elongation temperature and the driving operation (a thermal cycle step) is repeated.

When the thermal cycle step is repeated by a predetermined number of times to come to an end, the amplification product is transferred to the central well (to be referred to as 23B-M hereinafter) of the amplification reaction vessel 23B for a refining step. Subsequently, the refinement reagent is transferred from the reagent container 26A (e.g., the second well from left in FIG. 1) to the well 23B-M. The liquid in the well 23B-M is mixed and agitated by means of the pipette unit 13 to accelerate the reaction of adsorbing the sample nucleic acid to the magnetic beads. Then, the refining magnet mechanism of the amplification unit 3B is driven to approach the well and the liquid is agitated by means of the pipette unit 13. As a result, the magnetic beads where the target nucleic acid is adsorbed are gathered to the vicinity of the magnet. Under this condition, the liquid (which becomes unnecessary) that does not contain any magnetic beads is sucked by means of the pipette unit 13 and transferred to waste liquid depository 7 for waste disposal.

Thereafter, the reagent for releasing the nucleic acid from the magnetic beads is transferred from the reagent container 26A (e.g., the third well from left) to the well 23B-M to cause the reagent to react under the condition where the refining magnet mechanism is moved away from the well. (The liquid in the well is mixed and agitated by means of the pipette unit 13 in a similar manner.)

Subsequently, the refining magnet mechanism is brought closer to the well to gather the magnetic beads and the liquid part (containing the target nucleic acid) other than the magnetic beads is sucked by means of a pipette. Then, the liquid is transferred to the right side well (to be referred to as 23B-R hereinafter) in FIG. 1 in the amplification reaction vessel 23B.

Thereafter, the labeling reagent is transferred from the reagent container 26A (e.g., the fourth well from left in FIG. 1) to the well 23B-R. The labeling reagent contains a primer bonded to a fluorescent dye and PCR takes place between the primer and the sample nucleic acid so that the nucleic acid is labeled by the fluorescent dye.

When the pipette chip has to be replaced in the course of the amplification step of amplification, refinement and labeling, a program for controlling the pipette tip replacing operation is installed in the general control section 40 in advance.

(5) Transfer to Pre-Hybridization Sample Container

If the booked pre-hybridization sample container (assume here that it is 24C) is ready for use for the sample nucleic acid liquid obtained at the end of the above described step (4), the sample nucleic acid liquid is transferred to the container 24C by means of the pipette unit 13. If, on the other hand, the booked container 24C is not ready for use for the sample nucleic acid liquid, the sample nucleic acid liquid is held in the amplification reaction vessel until the booked pre-hybridization sample container 24C becomes ready for use. When the container 24C becomes ready for use, the sample nucleic acid liquid is transferred to the container 24C. After the transfer of the sample nucleic acid liquid, the used amplification reaction vessel is replaced with an unused one at a predetermined timing.

(6) Transfer to Hybridization Reaction Vessel

If the booked hybridization reaction vessel (assume here that it is vessel 25A) that is associated with the sample ID is ready for use or not is checked under the condition where the sample nucleic acid liquid is transferred to the booked pre-hybridization sample container.

If the vessel 25A is ready for use, the central processing unit 43 firstly starts controlling the temperature of the hybridization unit 5 to bring the unit 5 to a predetermined temperature suitable for the hybridization reaction (e.g., about 50° C.). Subsequently, the central processing unit 43 moves the pipette unit 13 to the reagent depository 6 and transfers the hybridization reagent from the rightmost well of a predetermined well (e.g., the rightmost well of the reagent container 26A) to the pre-hybridization sample container 24C. A cycle of suction and ejection is repeated in the well of the pre-hybridization sample container 24C by using the pipette unit 13 to accelerate the mixing of the sample nucleic acid liquid and the reagent liquid.

Subsequently, when the temperature of the hybridization unit 5 gets to a predetermined temperature level, the sample nucleic acid liquid is transferred from the pre-hybridization sample container to the hybridization reaction vessel by means of the pipette unit 13. When the hybridization reaction vessel (assume here that it is the vessel 25A) is not ready for use, the sample nucleic acid liquid is held in the pre-hybridization sample container until the hybridization reaction vessel becomes ready for use. Thereafter, when the hybridization reaction vessel becomes ready for use, the sample nucleic acid liquid is transferred to the vessel 25A. After the transfer of the sample nucleic acid liquid to the hybridization reaction vessel, the used pre-hybridization sample container is replaced by an unused one at a predetermined timing.

(7) Hybridization Reaction

The hybridization unit 5 operates to produce hybridization reactions of the sample nucleic acid liquids and the DNA microarrays by means of the hybridization reaction vessels 25A, 25B and 25C. The hybridization unit 5 includes units 5A, 5B and 5C of three lines that can operate independently. Each of the units 5A, 5B and 5C of the lines is provided with a temperature block adapted to hold the corresponding reaction vessel to a predetermined temperature level.

After containing the sample nucleic acid liquids in the hybridization reaction vessels, the hybridization unit 5 is held to the predetermined temperature level until a predetermined time elapses. While the sample nucleic acid liquids are held still in the hybridization reaction vessel of this embodiment, it is technically ease for those skilled in the art to provide a gene examination apparatus with a liquid drive unit and accelerate reactions by agitating the liquid contained in the apparatus. Therefore, if necessary, a gene examination apparatus according to the present invention may be provided with an arrangement for agitating liquid.

(8) Releasing Hybridization Reaction Vessels from Gene Examination Apparatus

After the above-described hybridization reaction of (7), the hybridization reaction vessels are released from the gene examination apparatus 1 by the user. Thereafter, the DNA microarrays in the hybridization reaction vessels are washed and dried. In another embodiment, the gene examination apparatus 1 is provided in the inside with a washing/drying section for washing/drying DNA microarrays and the hybridization reaction is followed by the processing by the washing/drying section. With such an arrangement, the washing/drying section has a liquid drive unit and a gas flow generation unit and the reagent containers 26A, 26B and 26C are provided with respective washing reagents.

After releasing the hybridization reaction vessels from the gene examination apparatus 1, unused ones are placed in the apparatus at a predetermined timing.

The signals of the dried DNA microarrays are read out by a fluorescence detector. In this embodiment, the fluorescence signal of a dried DNA microarray is read out to identify the type of the nucleic acid in a sample nucleic acid liquid only when the nucleic acid chain in the sample nucleic acid liquid is bonded to the nucleic acid chain anchored on the DNA microarray by way of a hybridization reaction.

Now, the booking method that takes an essential part of the present invention will be described below by referring to FIGS. 4 through 7. For the sake of convenience of description, a time table different from that of the gene examination apparatus 1 described in (1) through (8) above will be used. Note that the use of a different time table is only for the sake of convenience of description and the following technical description applies to any time table that is employed in a gene examination apparatus according to the present invention.

Figure 4:
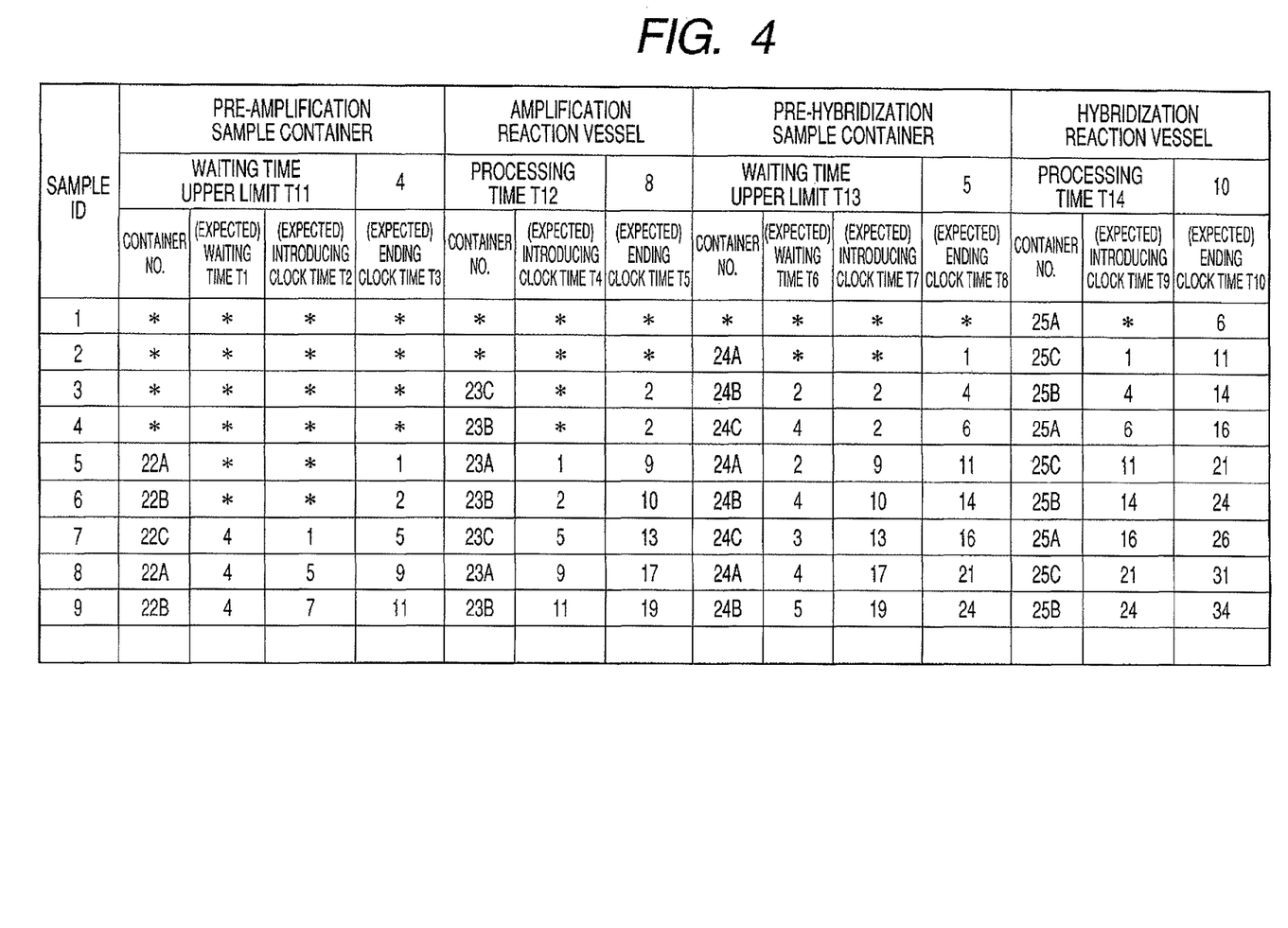
FIG. 4 is a schematic illustration of an advance booking table that may be prepared in the first embodiment of gene examination apparatus according to the present invention.

FIG. 4 is a booking table illustrating a processing schedule that the schedule management section can prepare.

Generation of a booking table and the process of generating a booking table is an essential part of preparation of a processing schedule in this embodiment of the present invention. Once a booking table is generated, the central processing unit 43 processes samples according to the booking table. As illustrated in FIG. 4, the user can arbitrarily specify the waiting time upper limit T11 that is the maximum waiting time until the processing of a sample, the processing time T12 and the processing time T14, taking the reaction conditions of each process into consideration. The times or clock times T1 through T10 and the vessel number of each process are determined by the gene examination apparatus 1.

As pointed out above, the user can arbitrarily specify the waiting time upper limit T11, the processing time T12 and the processing time T14. However, generation of the booking table is not indispensable if the processing schedule is prepared by taking the maximum waiting time until the processing of a sample to be handled into consideration. In other words, there may be an embodiment where samples are processed by referring to a booking table that is prepared in advance.

For instance, arrangements (1) and (2) described below are also within the scope of the present invention. Namely, (1) the gene examination apparatus 1 reads out the numerical values recorded on containers for time and (2) the gene examination apparatus 1 reads out the identification numbers recorded on containers and determines numerical values for time, referring to a predefined booking table from the inside of the apparatus 1 or the outside of the apparatus 1.

Figure 5:
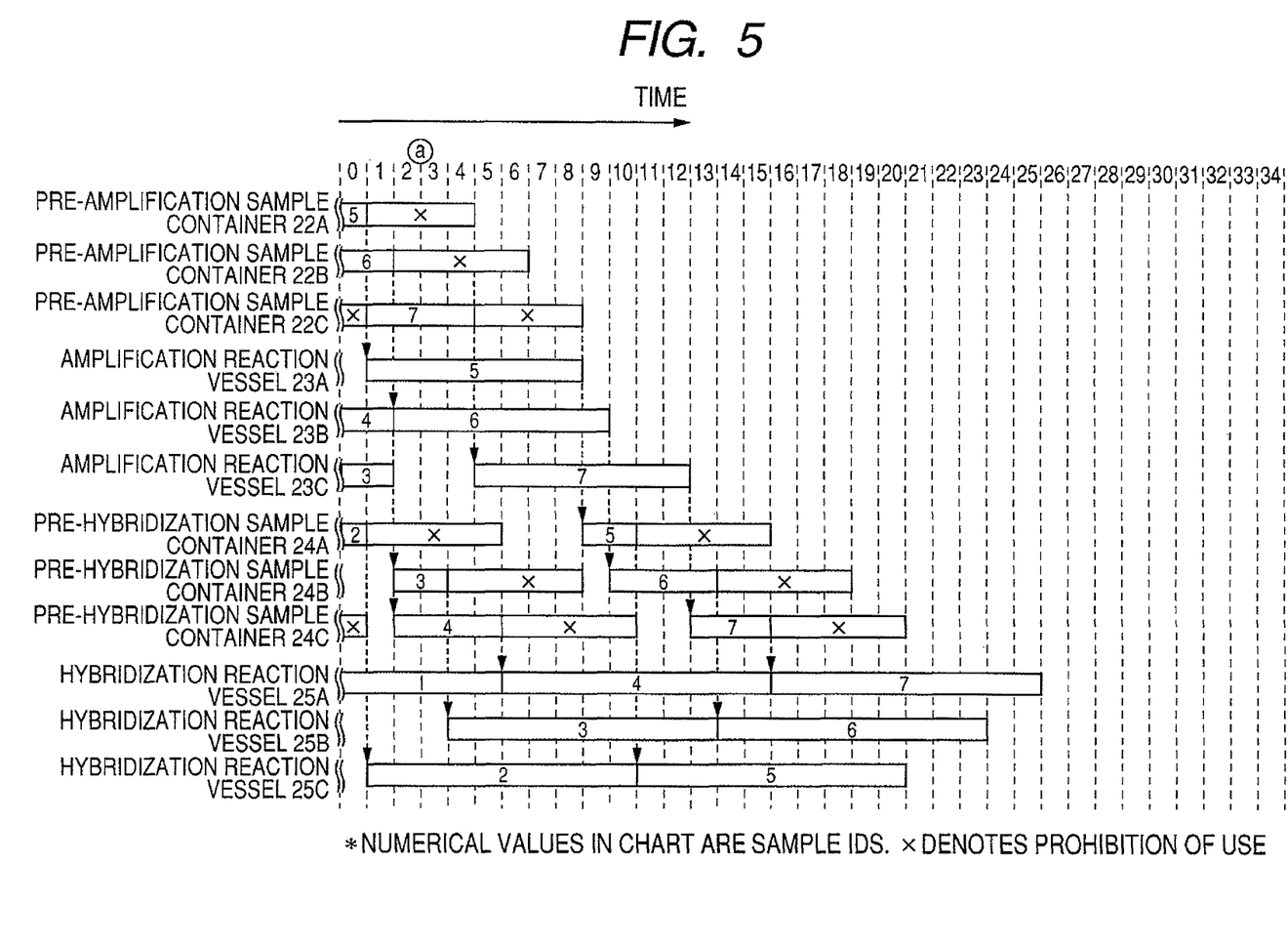
FIG. 5 is a timing chart before additional samples are booked.
Figure 6:
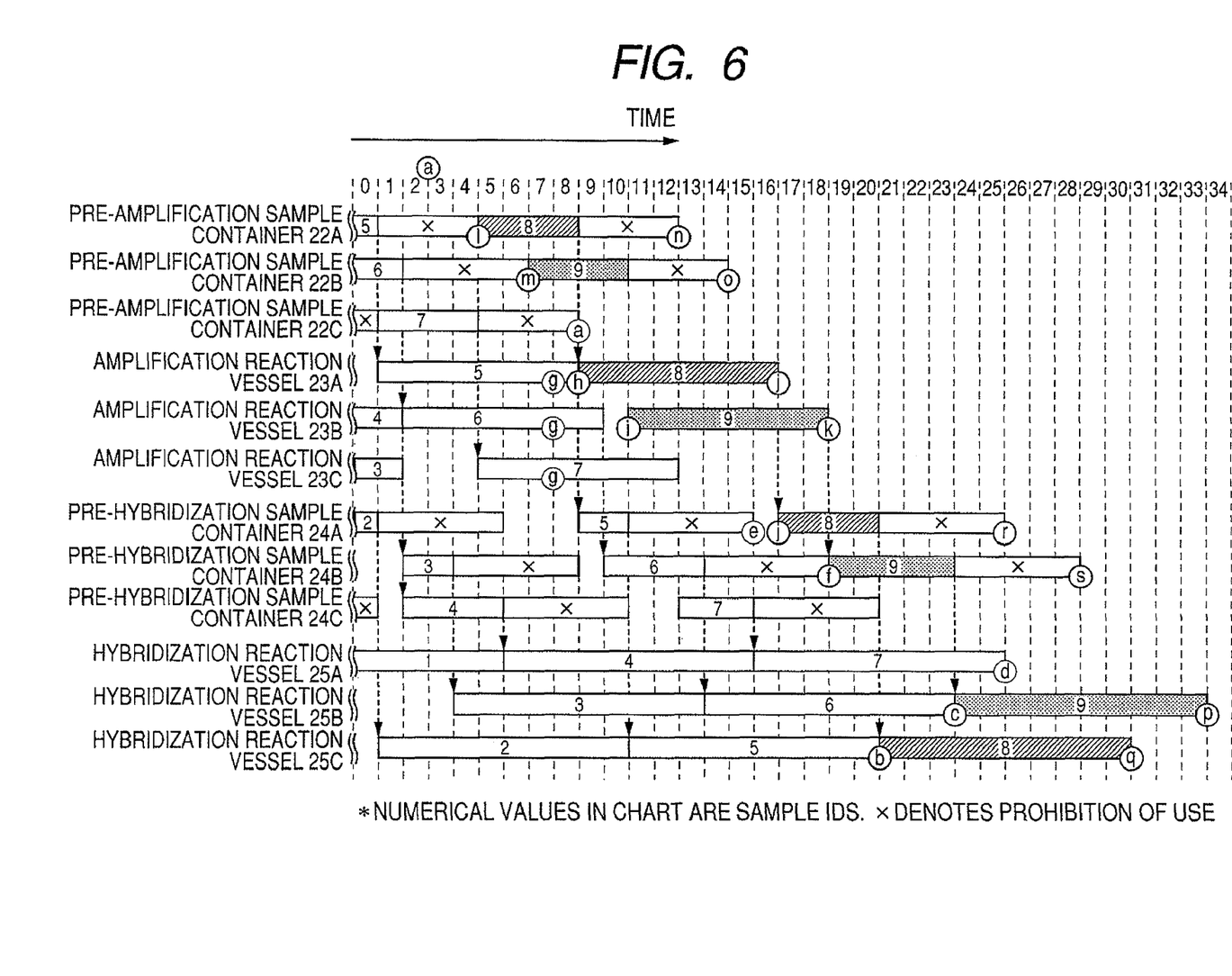
FIG. 6 is a timing chart after the additional sample are booked.

As an example, assume that a booking table for samples 1 through 7 is already determined and samples 8 and 9 are to be additionally introduced. Then, a booking table is generated in a manner as described below. FIGS. 5 and 6 are timing charts for generating a booking table before and after additional samples are booked, respectively. Assume that the booking tables are prepared so as to introduce additional samples 8 and 9 at clock time 3 (see "a" in FIGS. 5 and 6).

Figure 7:
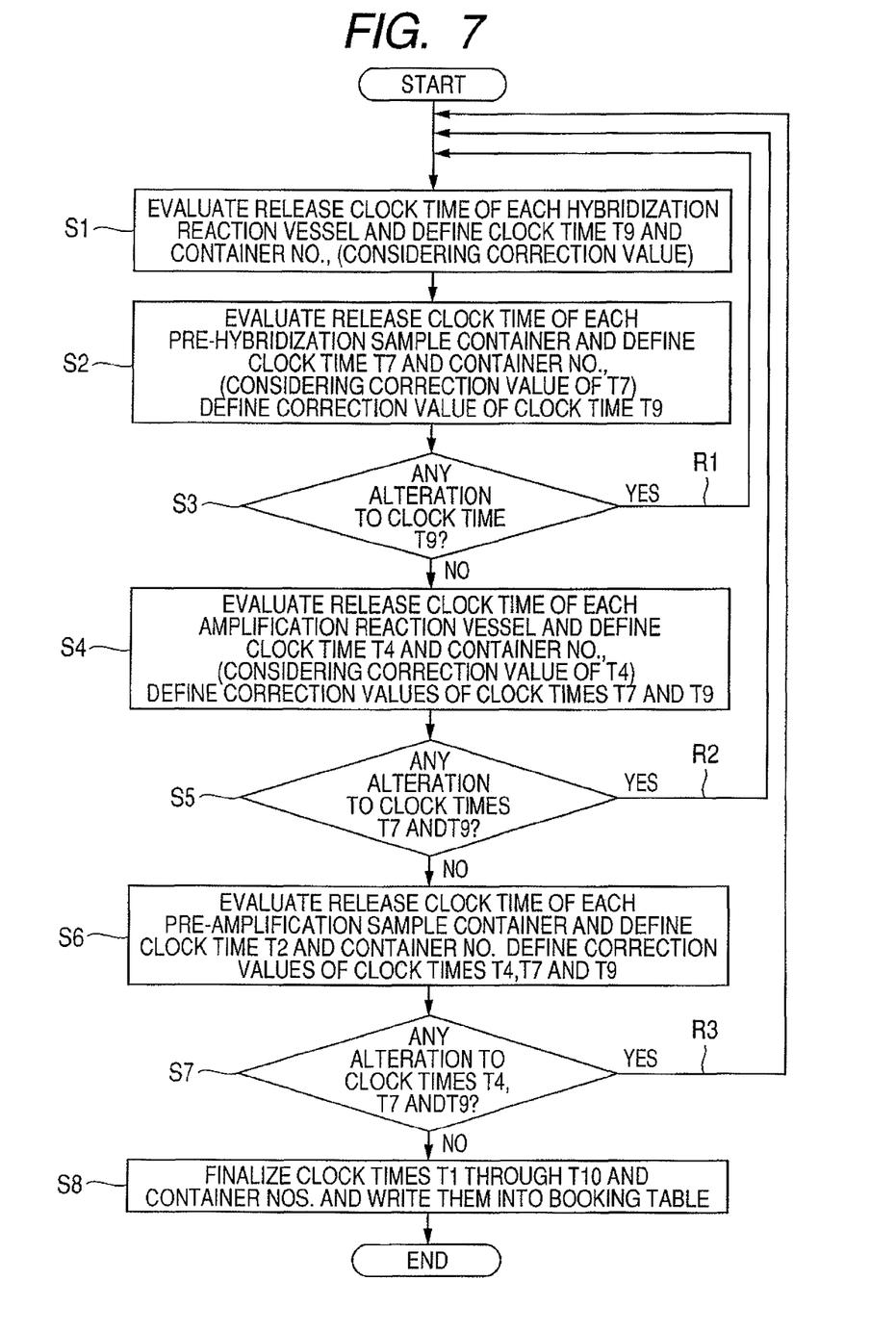
FIG. 7 is a flowchart for preparing an advance booking table.

Referring to FIG. 7, the clock time of releasing each hybridization reaction vessel is evaluated in Step S1. The hybridization reaction vessel that is released first and earliest is vessel 25C. The vessel 25C will be released at clock time 21 (see "b" in FIG. 6). The hybridization reaction vessel that is released next is vessel 25B. The vessel 25B will be released at clock time 24 (see "c" in FIG. 6). The hybridization reaction vessel that is released third is vessel 25A. The vessel 25A will be released at clock time 26 (see "d" in FIG. 6). On the basis of the above, the vessel 25C is specified for sample 8 and the clock time 21 is selected for the clock time T9 of the sample 8, whereas the vessel 25B is specified for sample 9 and the clock time 24 is selected for the clock time T9 of the sample 9. Note that the correction value is used for altering the clock time T9 when some other step is evaluated. However, the correction value is initially made equal to "0" so that it is not necessary to take the correction value into consideration in this example.

Then, the clock time of releasing each pre-hybridization sample container is evaluated in Step S2. Since the waiting time upper limit (maximum value) T13 is equal to time "5" for the pre-hybridization sample containers, a sample and a reagent are introduced into a pre-hybridization sample container after the clock time T9 less time "5". As a matter of course, the amplification unit is released early to improve the processing rate of the gene examination apparatus 1 if samples and reagents are introduced early. Therefore, priority is given to early introduction of samples and reagents. The container 24A is specified for sample 8 and clock time 16 is selected for the clock time T7 (see "e" in FIG. 6) of the sample 8, while the container 24B is specified for sample 9 and clock time 19 is selected for the clock time T7 (see "f" in FIG. 6) of the sample 9. Since the correction value of the clock time T7 is made equal to "0", it is not necessary to consider the correction value at this time point. Additionally, since it is not necessary to alter the clock time T9 for selecting a clock time value for the clock time T7, the correction value of the clock time T9 remains equal to "0" at this time point.

If the clock time T9 is altered in Step S3, the processing returns to Step S1, following Loop R1, and the above values are redefined. Since there is no alteration in this example, the processing proceeds to Step S4.

The releasing clock times of the amplification reaction vessels are evaluated in Step S4. The processing time T12 for amplification reaction is time "8". Therefore, if the sample can be introduced at the clock time T7 less time "8", that clock time is selected for clock time T4. If the sample cannot be introduced at that clock time, the clock time is altered and temporally moved backward within the allowable range for altering the clock times T7 and T9 or temporally forward, minimizing the alterations to the clock times T7 and T9. In this example, the container 23A is specified for the sample 8 and clock time 8 (see "g" in FIG. 6) is selected for the clock time T4 of the sample 8. However, since the container 23A is not released, the clock time T4 needs to be altered to clock time 9 (see "h" in FIG. 6).

As a result of the alteration, clock time 17 (see "j" in FIG. 6) is selected for the clock time T5. Therefore, the clock time T7 obviously needs to be altered to clock time 17 accordingly. Thus, "+1" is defined as the correction value of the clock time T7 of the sample 8. Then, the waiting time T6 is altered from time "5" to time "4" but the clock time T9 obviously can remain to be equal to clock time 21 (see "b" in FIG. 6). The vessel 23B is specified for the sample 9 and clock time 11 (see "i" in FIG. 6) is selected for the clock time T4 of the sample 9.

Since an alteration to the clock time T7 of the sample 8 is confirmed in Step S5, the processing returns to Step S1, following Loop R2. Since both the sample 8 and the sample 9 are evaluated at the same time in this example, the processing also returns to Step S1 for the sample 9 for reevaluation.

There is no change to the parameters in Step S1 because this is the second evaluation. The clock time T7 of the sample 8 is altered to clock time 17 (see "j" in FIG. 6) in Step S2 of the second evaluation. As a result of the evaluation in Step S4 of the second evaluation, the clock times T4, T7 and T9 can be defined without any contradiction.

Then, in Step S6, the release time of each of the pre-amplification sample containers is evaluated. Since the waiting time upper limit (maximum value) T11 of a pre-amplification sample container is time "4", the samples and the reagents are introduced into the respective pre-hybridization sample containers at clock time T4 less time "4". As a matter of course, the examination can be started early to improve the processing rate of the gene examination apparatus 1 when they are introduced early. Therefore, priority is given to an earlier introduction clock time. The container 22A is specified for the sample 8 and clock time 5 (see "1" in FIG. 6) is selected for the clock time T2 of the sample 8, while the container 22B is specified for the sample 9 and clock time 7 (see "m" in FIG. 6) is selected for the clock time T2 of the sample 9.

No alteration to the clock time T4, T7 or T9 is confirmed in Step S7. Then, in Step S8, all the items for the samples 8 and 9 are finalized in the booking table and the booking table is rewritten and updated.

While the time necessary for conveying the liquids and replacing any of the containers is disregarded in this embodiment, it is necessary to take such time into consideration for actual gene examination apparatus. However, a booking table that takes such time into consideration can be prepared according to the fundamental idea of the present invention.

As described above, the operation efficiency of the gene examination apparatus 1 of the embodiment can be improved by managing the schedule of operation thereof on the basis of the generated booking table. Additionally, the accuracy of processing samples of the gene examination apparatus 1 can be improved and degradation of samples and reagents can also be prevented by managing the schedule of operation thereof.

A sample nucleic acid liquid into which a reagent necessary for processing is introduced is used as sample to be introduced in the above description of the embodiment. However, for the purpose of the present invention, the reagent may be stored in a separate container and added to the sample nucleic acid liquid to be examined immediately before the processing operation. Not only samples but also reagents can show changes in the characteristics thereof when they are left at high temperature for a long time. As a typical example, it is known that, when polymerase enzyme to be used for a polymerase chain reaction (to be referred to as PCR hereinafter) is left at temperature higher than the room temperature for a long time, activity of the polymer enzyme is degraded to adversely affect the outcome of amplification. Therefore, when a reagent is stored in a separate container, it is desirable to keep information on the maximum waiting time of the reagent until the processing along with similar information of the sample.

Second Embodiment

Figure 8:
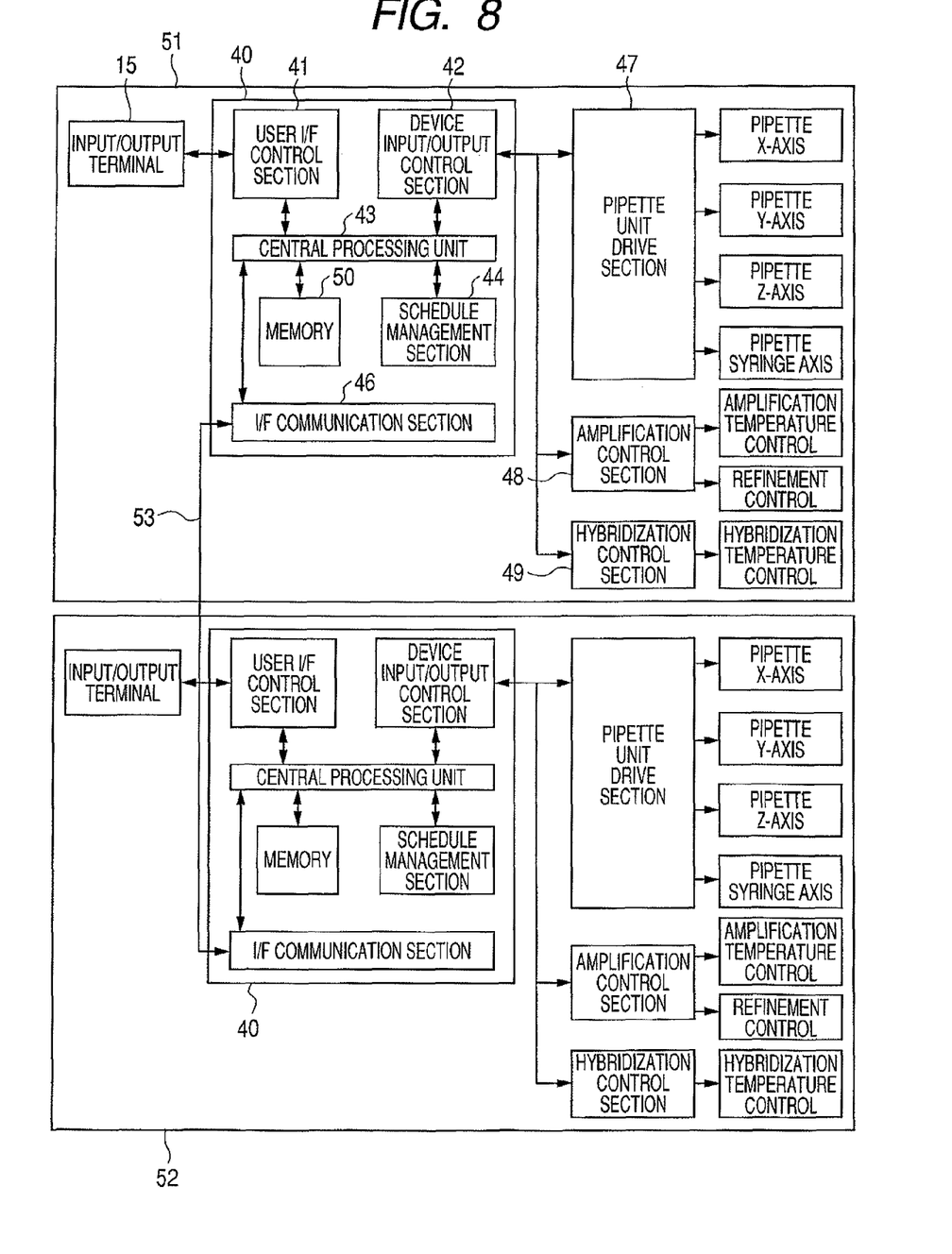
FIG. 8 is a schematic block diagram of the control system of a second embodiment of gene examination apparatus according to the present invention.

Referring to FIG. 8, gene examination apparatus 51 and 52 of the second embodiment have a configuration realized by providing the general control section 40 of the gene examination apparatus 1 of the first embodiment with a communication I/F section 46. The two gene examination apparatus 51 and 52 are connected to each other by way of a communication line 53 that is connected to the communication I/F sections thereof. For example, the gene examination apparatus 51 is operated as master control, while the gene examination apparatus 52 is operated as slave. The schedule management section 44 of the gene examination apparatus 51 prepares a booking table in such a way that the two gene examination apparatus 51 and 52 operate like a single gene examination apparatus. When a sample is to be moved between the gene examination apparatus 51 and 52 for some processing steps, the user is notified of the move by means of the input/output terminals 15 so that the user may manually move the container of the sample. However, as a matter of course, it is better for the processing efficiency to conduct the processing steps in the same apparatus, the algorithm of preparing a booking table is defined in such a way that priority is given to processing steps that are conducted in the same apparatus. For example, a lower limit is defined for the waiting time when a sample is to be moved between the apparatus 51 and 52. When the waiting time between processing steps exceeds the lower limit, the next processing unit in the same apparatus or in the other apparatus is assigned to the sample.

Additionally, the operation efficiency of the schedule of a gene examination process can be further improved when this embodiment is made to also include a conveyance system for automatically conveying a sample and a container between the two apparatus 51 and 52 so that the general control section 40 controls the conveyance of the sample and the container. Any of various means easily conceivable to those skilled in the art may be used to configure the conveyance system and control the conveyance of samples and containers.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2006-213275, filed Aug. 4, 2006, which is hereby incorporated by reference herein in its entirety.

What is claimed is:

1. A sample processing apparatus comprising:
a processing unit configured to process samples and having at least three lines, each line including a plurality of processing sections having individual processing abilities and a waiting section for allowing a sample to be processed by one of the processing sections to temporarily wait, at least three of the plurality of processing sections being capable of independently performing processing operations;
a pipette unit configured to transfer liquid from one container to another container placed in different sections;
a memory configured to store information on maximum waiting times tolerable for respective samples to be introduced into the plurality of processing sections;
a scheduling section programmed to prepare a processing schedule for the samples according to the information on maximum waiting times stored in the memory so that a sample in a waiting section of one line can be transferred to a processing section of another line by means of the pipette unit to maximize the operation efficiency of processing the samples by using the plurality of processing sections without damaging the accuracy of processing results,
wherein the scheduling section is further programmed to alter the schedule according to an upper limit of waiting time for a newly added sample, and
wherein the alteration of the schedule is performed by evaluating a clock time of releasing a container for each step of the schedule before being altered, along with the upper limit of waiting time for the newly added sample, and by correcting the already prepared processing schedule for the samples based on the evaluation.

2. The apparatus according to claim 1, further comprising:
an input unit configured to input the information on maximum waiting times to the memory.

3. The apparatus according to claim 1, further comprising:
a communication unit configured to communicate with another sample processing apparatus, wherein
the scheduling section determines at least a clock time for introducing a sample, a processing section configured to process a sample out of the plurality of processing sections or a waiting time of a sample for other than a reaction in the plurality of sample processing apparatuses.

4. The apparatus according to claim 1, wherein the scheduling section generates a booking table, combining a clock time for introducing a sample and a processing section configured to process the sample having the clock time for introduction.

5. The apparatus according to claim 4, wherein
when a sample to be introduced into the apparatus is added, the scheduling section alters the booking table according to an upper limit of waiting time for other than a reaction, a reaction time of the added sample and a remaining time of reaction of another sample being processed in the processing section.

* * * * *